United States Patent [19]

Pravoverov et al.

[11] 4,273,137
[45] Jun. 16, 1981

[54] ELECTRICAL CONDUCTOR FOR IMPLANTATION INTO HUMAN BODY

[76] Inventors: Nikolai L. Pravoverov, ulitsa Pervomaiskaya, 16, kv. 4, Istra Moskovskoi; Ravil N. Nazyrov, MIZ, dom 31-1, Mozhaisk; Sergei S. Grigorov, prospekt Vernadskogo, 105, korpus 2, kv. 81, Moscow; Lidia S. Turova, ulitsa Jubileinaya, 13, kv. 59, Istra Moskovskoi, all of U.S.S.R.

[21] Appl. No.: 104,390

[22] Filed: Dec. 17, 1979

[51] Int. Cl.³ .............................................. A61N 1/04
[52] U.S. Cl. ................................................... 128/784
[58] Field of Search ..................... 128/419 P, 784–786

[56] References Cited

U.S. PATENT DOCUMENTS

| 3,035,583 | 5/1962 | Hirsch et al. | 128/419 P |
| 4,033,355 | 7/1977 | Amundson | 128/786 |
| 4,198,991 | 4/1980 | Harris | 128/419 P |

*Primary Examiner*—William E. Kamm
*Attorney, Agent, or Firm*—Steinberg & Raskin

[57] ABSTRACT

An electrical conductor for implantation into human body is made as a braid woven of fibers and enclosed into an insulating sheath. Each fiber is a tube made of a high-strength corrosion-proof nontoxic alloy filled with a highly conductive alloy or metal.

4 Claims, 2 Drawing Figures

ELECTRICAL CONDUCTOR FOR IMPLANTATION INTO HUMAN BODY

FIELD OF INVENTION

This invention relates to medical instrument making, to electrostimulators of tissue and organs and, in particular, to electrical conductors for implantation into human body.

PRIOR ART

An electrical conductor for implantation into human body is intended for transmission of electrical pulses from a power source to a body organ. This electrical conductor is a vital element of the design of an electrode. Such a conductor should be durable, resist corrosion in the medium of a living organism, non toxic and sufficiently conductive electrically so that electrical losses in this conductor are minimized.

There is known an electrical conductor for implantation into human body, employed in a bipolar endocardiac electrode manufactured by Medtronte as 6901 model.

This known conductor is made of a nickel alloy as a wovel cylindrical spring which makes the conductor extremely flexible. If the conductor is 58 cm long, its resistance is 75 ohms, when it is 85 cm long, the resistance is 105 ohms.

This conductor is durable, sufficiently corrosion-proof, but its resistance is high and the energy accumulated in the power source of the stimulator is inefficiently wasted, thus reducing the life time of the implanted instrument.

There is also known an electrical conductor for implantation into human body, made as an insulating sheath holding woven conducting fibers. Each fiber is made as a tube of carbon, filled with an elastic material (barium sulfate) (cf., for example, USSR Inventor's Certificate No. 291,404, 1968).

However, the tenacity of such a conductor which is 2–4 mm in diameter and 50–150 cm long is 5–8 kg (corresponds to $\sigma_B = 2$ kg/mm$^2$) and the resistance is about 100 ohms. This means that such a conductor cannot be used for long-term exploitation for electrostimulation of tissues and organs because the strength and electrical conductivity thereof are insufficient.

BRIEF DESCRIPTION OF INVENTION

It is an object of this invention to increase the reliability of an electrical conductor for implantation into human body.

Another object of this invention is to ensure high quality mechanical properties of an electrical conductor for implantation into human body.

These objects are achieved in that in an electrical conductor for implantation into human body, comprising an insulating sheath and conducting fibers placed therein and made as tubes with a filler, according to the invention, the tubes are made of a high-strength, corrosion-proof nontoxic alloy, whereas the filler is made of a highly conductive metal or alloy.

It is advisable that tubes are made of stainless steel, whereas the filler is made of silver or silver conductor alloys.

It is possible that tubes are made of cobalt alloys and the filler of silver or silver conductor alloys.

Besides, it is useful that tubes are made of cobalt alloys or stainless steels and the filler of copper or conductive copper alloys.

The electrical conductor made in accordance with the present invention possesses high electrical and mechanical characteristics which ensures durable and reliable operation when implanted into human body. Besides, low electrical resistance of the conductor permits sparing expenditure of the power source energy, thus extending the life time of the stimulator and the period between operations to change the electrostimulator which has exhausted its power source.

BRIEF DESCRIPTION OF DRAWINGS

The invention will now be described in greater detail with reference to a specific embodiment thereof, taken in conjunction with the accompanying drawings, wherein.

DETAILED DESCRIPTION OF THE INVENTION

An electrical conductor for implantation into human body in this embodiment is shown in conjunction with elements of an endocardiac electrode, since it is in case of stimulation of the cardiac muscle the electrical conductor operates in the most trying conditions as far as strength and reliability is concerned.

With 70 beats per minute the heart does 36.8 million contractions per annum. Besides, the synchronous movements of auricles and breathing contactions should not be left out. The motion of electrodes, therefore, is extremely complex. Such electrodes rated for 10 year service are subjected to long-term mechanical bending (up to $4 \cdot 10^8$ alternating cycles), twisting and tensile loads.

Figure 2:
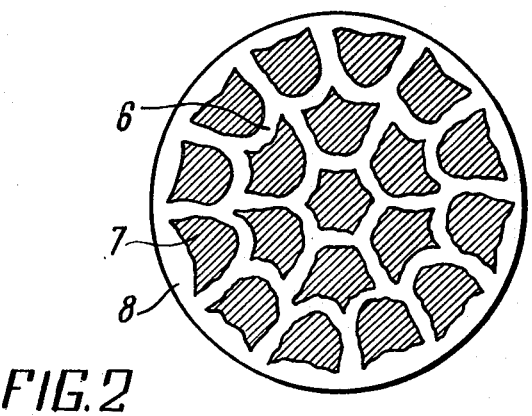
FIG. 2 illustrates a cross-sectional enlarged view of an electrical conductor of FIG. 1, devoid of the insulating sheath.
Figure 1:
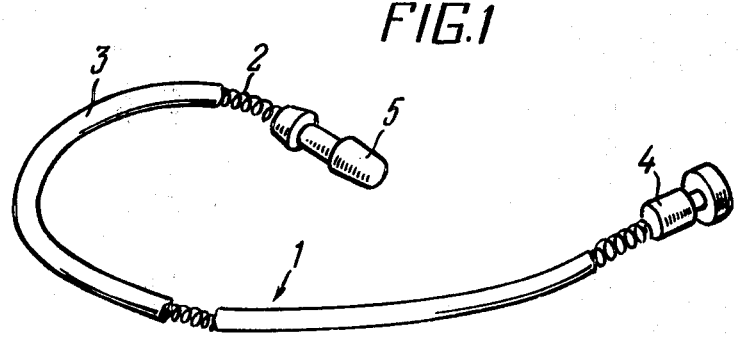
FIG. 1 illustrates an electrical conductor for implantation into human body, according to the invention, provided with contact and distal tips of an electrocardiostimulator.

An electrical conductor 1 (FIGS. 1 and 2) comprises a flexible braid 2 composed of conductive fibers, coiled into a single-thread or multi-thread spiral and placed into an insulating elastic sheath 3 made of silicone rubber. The sheath 3 protects the conductor against agressive biological medium and prevents current leakages. The spiral winding of the conductor provides a space for a mandrin required, for example, for transvenous implantation. The ends of the conductor are free from the insulating sheath 3 and one is connected to a distal tip 4 of the electrode and the other to a contact tip 5.

Each fiber of the braid 2 is a tube 6 made of a high-strength, corrosion-proof nontoxic alloy with a filler 7 which is a highly conductive metal or alloy. In order to keep the braid 2 from separating into single fibers an auxiliary sheath 8 is provided to tightly wrap the braid 2. The sheath 8 is made of the same material as the tubes 6.

The material of the tubes 6 can be stainless steel having the following composition in weight percent:

| | | |
|---|---|---|
| carbon | <0.12 | |
| manganese | 1–2 | (1) |
| chrome | 17–19 | |
| nickel | 9–11 | |
| titanium | (c-0.02).5–0.7 | | or stainless steel of the following composition, in weight percent:

| | | |
|---|---|---|
| carbon | <0.08 | |
| manganese | 1–2 | |
| chrome | 17–19 | (II) |
| nickel | 9–11 | |
| titanium | 5.0–0.6 | |
| selenium or tellurium | 0.18–0.35 | |
| iron | the balance | | or a cobalt alloy of the following composition, in weight percent:

| | | |
|---|---|---|
| carbon | 0.05 | |
| silicon | 0.5 | |
| manganese | 1.8–2.2 | |
| cobalt | 39–41 | (III) |
| nickel | 15–17 | |
| chrome | 26–27 | |
| molybdenum | 6.4–7.4 | |
| tantalum | from 1 to 3 | | or steel of the following composition, in weight percent:

| | | |
|---|---|---|
| carbon | 0.15 | |
| manganese | 2 | |
| nickel | 15 | |
| chrome | 20 | (IV) |
| cobalt | 40 | |
| molybdenum | 7 | |
| beryllium | 0.04 | |
| iron | the balance. | |

The material of the filler 7 can be silver or slightly doped conductive silver-based alloys, for example, an alloy of the following composition, in weight percent:

| | | |
|---|---|---|
| palladium | 0.5 | |
| nickel | 0.15 | |
| magnesium | 0.05 | (V) |
| silver | the balance, | | or an alloy of the following composition in weight percent:

| | | |
|---|---|---|
| nickel | 0.2 | |
| magnesium | 0.3 | (VI) |
| siver | the balance, | | or an alloy of the following composition, in weight percent:

| | | |
|---|---|---|
| copper | 2.0 | |
| nickel | 2.0 | (VII) |
| silver | the balance. | |

The material of the filler 7 can also be copper comprising not more than 0.1–0.04 weight percent of admixtures or slightly doped copper alloys, for example, an alloy of the following composition, in weight percent:

| | | |
|---|---|---|
| chrome | 0.3 | |
| zirconium | 0.2 | (VIII) |
| cooper | the balance. | |

In accordance with the present invention an electrical conductor (two-thread spiral) was made where the tubes 6 and the sheath 8 were of stainless steel having composition (I) and the filling of the tubes 6 was of the silver-based conductive alloy having composition (V). The external diameter of the sheath 8 was 0.2 mm, the diameter of the spiral 1.7 mm, the length of the spiral-coiled conductor—85 cm. Such a conductor had 3.2 ohms resistance. The conductor was tested for durability. This durability (the number of cycles till destruction) was $1.08 \cdot 10^8$ cycles with the initial load of 44.4 kg/mm$^2$ and the cyclic load of 3,000 bendings per minute.

What is claimed is:

1. An electrical conductor for implantation into human body, comprising: an insulating sheath; conductive fibers placed in said insulating sheath; tubes made of high-strength, corrosion-proof, nontoxic alloy, forming said fibers; a filler of said tubes made of a highly electrically conductive metal or alloy.

2. An electrical conductor as claimed in claim 1, wherein said tubes are made of stainless steel and said filler of silver or silver-based conductive alloys.

3. An electrical conductor as claimed in claim 1, wherein said tubes are made of cobalt-based alloys and said filler is made of silver or silver-based conductive alloys.

4. An electrical conductor as claimed in claim 1, wherein said tubes are made of cobalt-based alloys or stainless steels and said filler is made of copper or copper-based conductive alloys.

* * * * *